United States Patent [19]

Caspari et al.

[11] Patent Number: 4,496,495
[45] Date of Patent: Jan. 29, 1985

[54] STABILIZATION OF PHOSPHORODITHIOIC ACID DIESTERS

[75] Inventors: Gunter J. Caspari, Wheaton; Steven E. Lindberg, Wheatland Township, Will County, both of Ill.

[73] Assignee: Standard Oil Company (Indiana), Chicago, Ill.

[21] Appl. No.: 457,450

[22] Filed: Jan. 12, 1983

[51] Int. Cl.$^3$ .............................................. C07F 9/165
[52] U.S. Cl. ............................................................ 260/989
[58] Field of Search ............................................... 260/989

[56] References Cited

U.S. PATENT DOCUMENTS 3,361,668  1/1968  Wiese ................................... 260/981
3,668,282  6/1972  Below ................................... 260/989
4,083,899  4/1978  Demarcq ............................. 260/981

FOREIGN PATENT DOCUMENTS 1228528  4/1971  United Kingdom ................ 260/980

Primary Examiner—Anton H. Sutto
Attorney, Agent, or Firm—Richard A. Kretchmer; William T. McClain; William H. Magidson

[57] ABSTRACT

Diesters of phosphorodithioic acid are stabilized against thermal decomposition by the addition of small amounts of a stabilizer which is selected from the group consisting of ammonia, ammonium carbonate, ammonium salts of carboxylic acids, the oxides, hydroxides and carbonates of lithium, sodium, potassium, rubidium, cesium, berylium, magnesium, calcium, strontium and barium, and mixtures thereof.

20 Claims, No Drawings

STABILIZATION OF PHOSPHORODITHIOIC ACID DIESTERS

BACKGROUND OF THE INVENTION

1. Field of the Invention

This invention relates to a method for improving the thermal stability of phosphorodithioic acid diesters. More particularly, it relates to a method for stabilizing such materials which involves the addition of a minor amount of a stabilizer.

2. Description of the Prior Art

The preparation of phosphorodithioic acid diesters by the reaction of a phosphorus sulfide with alcohols or phenols is a well known process which can be described in general terms by the following equation where R represents a hydrocarbyl or substituted hydrocarbyl group and phosphorus pentasulfide is employed as the phosphorus sulfide starting material:

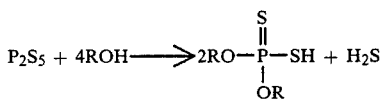

The phosphorodithioic acid diesters produced by this process are typically accompanied by small amounts of other related materials, such as $P(S)(OR)_2(H)$, $P(S)(OR)_2(SR)$, $P(S)(OR)_3$, $P(O)(OR)_2(SH)$, $P(S)(OR)(OH)_2$, $P(S)(OR)(OH)(SH)$, $(RO)_2(S)P\text{-}S\text{-}P(S)(OR)_2$, and $(RO)_2(S)P\text{-}SS\text{-}P(S)(OR)_2$. In addition, small amounts of elemental sulfur are frequently observed as a by-product of the above-mentioned reaction.

The phosphorodithioic acid diesters can be converted to their corresponding metal salts by reaction with basically reacting metal compounds such as oxides, hydroxides or carbonates. These metal salts are known to be useful as antioxidants and corrosion inhibitors. The zinc salts of phosphorodithioic acid diesters are particularly useful as additives for crankcase lubricants for use in internal combustion engines since they are excellent antioxidants and are also highly effective in reducing the wear and corrosion of the lubricated engine components. For example, these zinc salts protect corrosion-susceptible nonferrous metal components of the engine, such as bearings, against corrosive contaminants in the lubricating oil. Such contaminants are primarily acidic products of oil oxidation and acidic products from the combustion of fuel which blow past the piston rings and into the crankcase. It is believed that the zinc salts of the phosphorodithioic acid diesters function as corrosion inhibitors for nonferrous engine parts, such as copper-lead or lead-bronze faced bearings, by reacting chemically with the surface of these parts to form a protective corrosion-resistant film.

Although the zinc salts of phosphorodithioic acid diesters are highly desirable antioxidants and wear and corrosion inhibitors for use in crankcase lubricants, it is also desirable to use no more of these phosphorus-containing compounds than is necessary to provide the required protection against oxidation, wear and corrosion. This, of course, is a partial consequence of the fact that such additives are relatively expensive in comparison with the mineral oils which are typically used as lubricant base oils. More important, however, is the fact that phosphorus is considered to be harmful to the catalytic converters which are currently employed to control the emission of hydrocarbons, carbon monoxide and nitrogen oxides from automotive engines. In view of this, it is desirable to minimize the phosphorus content of crankcase oils for internal combustion engines which are in automotive service since some of the phosphorus from an engine's lubricant ultimately finds its way into the catalytic converter by way of oil leakage past the piston rings and into the combustion chambers of the engine.

Zinc salts of phosphorodithioic acid diesters wherein at least one of the two ester groups is derived from a secondary alcohol are typically more active as antioxidants and as corrosion and wear inhibitors than the corresponding materials wherein the ester groups are derived from primary alcohols. The use of these more active zinc salts is desirable in the preparation of crankcase lubricants since they permit the formulation of lubricant compositions which have a lower phosphorus content than would be possible with the less active materials. Unfortunately, the phosphorodithioic acid diesters which are obtained by the reaction of phosphorus sulfides with secondary alcohols are usually much less stable than the corresponding materials which are derived from primary alcohols. Further, the manufacture of the zinc salts of these secondary alcohol derivatives is frequently difficult because of this lesser stability. As a consequence, there is a need for a method of stabilizing the phosphorodithioic acid diesters which are derived from the reaction of phosphorus sulfides with secondary alcohols.

U.S. Pat. No. 3,361,668, issued to Wiese on Jan. 2, 1968, discloses that when phosphorodithioic acid diesters are prepared by the reaction of an alcohol or phenol with phosphorus pentasulfide, a product of reduced coloration can be obtained either by adding a small amount of an amine to the alcohol or phenol prior to reaction with the phosphorus pentasulfide or by adding a small amount of the amine to the diester subsequent to its formation. This patent does not, however, suggest that the thermal stability of a diester of phosphorodithioic acid could be improved by any means and does not suggest the use of any materials other than amines to improve the properties of such a phosphorodithioic acid derivative.

U.S. Pat. No. 4,083,899, issued to Demarcq on Apr. 11, 1978, discloses that the preparation of phosphorodithioic acid diesters by reaction of phosphorus pentasulfide with alcohols or phenols can be catalyzed by the use of a wide variety of nitrogen-containing compounds in an amount which ranges from 0.01 to 10% by weight based on the alcohol or phenol. Similarly, British patent specification No. 1,228,528 discloses that from 1 ppm to 1% by weight of ammonia can be used to catalyze the reaction of phosphorus sulfides with alcohols and phenols. In addition, U.S. patent application Ser. No. 242,107 by Sabol et al. teaches that the neutralization reaction between a phosphorodithioic acid diester and a basically reacting zinc compound can be catalyzed by ammonia and ammonia-yielding compounds. However, these references fail to suggest that the thermal stability of a diester of phosphorodithioic acid could be improved by any means.

SUMMARY OF THE INVENTION

The present invention is directed to the discovery that diesters of phosphorodithioic acid can be stabilized against thermal decomposition by the addition of small amounts of certain bases.

One embodiment of the invention is a method for stabilizing a phosphorodithioic acid diester which comprises adding to said diester a stabilizer which is selected from the group consisting of ammonia, ammonium carbonate, ammonium salts of carboxylic acids, the oxides, hydroxides and carbonates of lithium, sodium, potassium, rubidium, cesium, berylium, magnesium, calcium, strontium and barium, and mixtures thereof, wherein the amount of said stabilizer is effective to increase the thermal stability of the phosphorodithioic acid diester.

Another embodiment of the invention is the composition prepared by the process which comprises mixing a phosphorodithioic acid diester with a stabilizer which is selected from the group consisting of ammonia, ammonium carbonate, ammonium salts of carboxylic acids, the oxides, hydroxides and carbonates of lithium, sodium, potassium, rubidium, cesium, berylium, magnesium, calcium, strontium and barium, and mixtures thereof, wherein the amount of said stabilizer is effective to increase the thermal stability of the phosphorodithioic acid diester.

An object of this invention is to provide a method for stabilizing phosphorodithioic acid diesters.

Another object of this invention is to provide a method for stabilizing phosphorodithioic acid diesters which are derived from the reaction of a phosphorus sulfide with at least one compound selected from the group consisting of alcohols and phenols.

Another object of this invention is to provide a method for stabilizing phosphorodithioic acid diesters which are derived from the reaction of phosphorus pentasulfide with secondary aliphatic alcohols.

A further object of this invention is to provide a phosphorodithioic acid diester composition of increased thermal stability.

A still further object of this invention is to provide a phosphorodithioic acid diester composition which is more easily converted to its corresponding metal salts.

DETAILED DESCRIPTION OF THE INVENTION

We have found that phosphorodithioic acid diesters can be stabilized against thermal decomposition by the addition of small amounts of a stabilizer which is selected from the group consisting of ammonia, ammonium carbonate, ammonium salts of carboxylic acids, the oxides, hydroxides and carbonates of lithium, sodium, potassium, rubidium, cesium, berylium, magnesium, calcium, strontium and barium, and mixtures thereof. Suitable ammonium salts of carboxylic acids for use in this invention preferably contain from 1 to about 50 carbon atoms and include, but are not limited to, ammonium acetate, ammonium benzoate, ammonium citrate and ammonium propionate. If desired, amines can also be utilized as the stabilizer in the practice of this invention.

In the practice of this invention, the stabilizer is added to the phosphorodithioic acid diester in a minor amount which is effective to increase the thermal stability of the diester. Desirably, the amount of stabilizer is in the range from about 0.0001 to about 0.2 mole per mole of phosphorodithioic acid diester. Preferably, however, the amount of stabilizer is in the range from about 0.001 to about 0.05 mole per mole of phosphorodithioic acid diester. It will be appreciated, however, that the precise amount of stabilizer which is required will vary and will be a function of the specific phosphorodithioic acid diester composition which is being treated. The use of an amount of stabilizer in excess of the amount required to provide the required thermal stability is ordinarily undesirable since such an excess would merely represent an unnecessary contaminant or impurity in the phosphorodithioic acid diester.

In the practice of this invention, the stabilizer can be used to improve the thermal stability of substantially pure phosphorodithioic acid diesters. In addition, the stabilizer can also be used to improve the thermal stability of phosphorodithioic acid diesters which are mixed with diluents which include, but are not limited to, mineral oils and conventional organic solvents such as hexane, heptane, diethyl ether, petroleum ether, benzene, toluene and xylene. Such diluents are, preferably, substantially inert.

The phosphorodithioic acid diesters for use in the practice of this invention are desirably obtained from the reaction of a phosphorus sulfide with at least one compound selected from the group consisting of alcohols and phenols. However, in view of the fact that the phosphorodithioic acid diesters which are obtained from secondary or tertiary alcohols are usually less stable than those which are derived from primary alcohols, the method of this invention is particularly useful for the stabilization of these less stable materials. As a result of these stability considerations, the phosphorodithioic acid diesters for use in the practice of this invention are preferably derived from the reaction of a phosphorus sulfide with a secondary aliphatic alcohol or a mixture of compounds selected from the group consisting of alcohols and phenols which comprises at least one secondary aliphatic alcohol. Although not necessary, the phosphorodithioic acid diesters are preferably derived from the reaction of a phosphorus sulfide with monohydric alcohols or phenols.

The zinc salts of phosphorodithioic acid diesters which contain at least about 6 carbon atoms are generally preferred for use as lubricant additives. Consequently, the phosphorodithioic acid diesters from which these zinc salts are prepared also contain at least about 6 carbon atoms. In addition, the phosphorodithioic acid diesters from which these salts are derived are desirably prepared from the reaction of a phosphorus sulfide with at least one monohydric aliphatic alcohol.

Alcohols and phenols which are useful in the preparation of the phosphorodithioic acid diesters of this invention desirably contain from 1 to about 50 carbon atoms and can contain a variety of substituents which include, but are not limited to, nitro, alkoxy, halo and carboalkoxy, groups. Examples of suitable alcohols include, but are not limited to, methanol, ethanol, 1-propanol, 2-propanol, 4-methyl-2-pentanol, 1-pentanol, 8-methyl-1-nonanol, 6-methyl-1-heptanol, 1-butanol, 2-methyl-2-propanol, 1-decanol, 2-ethyl-1-hexanol, 1,6-hexanediol, phenol, chlorophenol, bromophenol, cresol, propylphenol, butylphenol, heptylphenol, octylphenol and nonylphenol.

Any phosphorus sulfide which will yield phosphorodithioic acid diesters when reacted with alcohols or phenols can be used to prepare the phosphorodithioic acid diesters of this invention. However, phosphorus pentasulfide, $P_2S_5$, is highly preferred for use in the preparation of the phosphorodithioic acid diesters of this invention for reasons of low cost, availability and satisfactory reactivity. Commercial phosphorus pentasulfide is typically somewhat impure and contains significant amounts of other phosphorus sulfides. Nevertheless, such commercial phosphorus pentasulfide is highly satisfactory for use in preparing the subject phosphorodithioic acid diesters.

The phosphorodithioic acid diesters of this invention are conveniently prepared by the reaction of a phosphorus sulfide with at least one alcohol or phenol at a suitable temperature according to conventional methods, such as that which is set forth in U.S. Pat. No. 2,862,947 to Goldsmith. For example, these diesters are commonly prepared by slurrying phosphorus pentasulfide in an inert hydrocarbon solvent and adding an appropriate amount of an alcohol or phenol to the resulting slurry. When a monohydric alcohol or phenol is employed, the mole ratio of alcohol or phenol to phosphorus pentasulfide is usually in the range from about 3 to about 5, or desirably about 4. Preferably, the amount of phosphorus pentasulfide employed is such that a small amount of unreacted phosphorus sulfide is still present upon completion of the reaction. Accordingly, a slight stoichiometric excess of alcohol or phenol can be used and, preferably, about 4.1 to about 4.5 moles of alcohol or phenol is used per mole of phosphorus pentasulfide. The reaction can be carried out at temperatures in the range from about 20° to about 250° C., although preferred temperatures are usually in the range from about 60° to about 150° C. If desired, the reaction can be carried out under an inert atmosphere, such as nitrogen, in order to preclude any possible decomposition as a consequence of air oxidation. Depending on the identity of the reactants, the purity of the reactants, the concentrations of the reactants, and the temperature, the reaction can usually be completed in about 10 minutes to about 20 hours. Reaction parameters are selected and controlled in a conventional manner to obtain optimum results.

Completion of the reaction between the phosphorus sulfide and the alcohol or phenol can be conveniently determined either by monitoring the specific gravity of the reaction mixture or by monitoring the evolution of hydrogen sulfide. The stabilizer of this invention can be added to the phosphorodithioic acid diester at any time subsequent to completion of this reaction. If desired, the reaction product can be stripped of volatiles, such as unreacted alcohols or phenols, by conventional techniques which include treatment with a stream of an inert gas such as nitrogen at appropriate temperatures and pressures. Unreacted phosphorus sulfides and any other solids can be conveniently removed from the usually liquid product by centrifugation or filtration.

Although the present invention is not to be so limited, we have found that small amounts of phosphoric and polyphosphoric acids catalyze the decomposition of phosphorodithioic acid diesters. In addition, phosphoric and polyphosphoric acids are typical contaminants of phosphorus sulfides, such as phosphorus pentasulfide, and are formed by hydrolysis of the phosphorus pentasulfide upon contact with water. As a consequence of the ubiquitous presence of water, it is essentially impossible to obtain phosphorus pentasulfide which is free of phosphoric and polyphosphoric acids. Since the stabilizer of this invention consists of a group of materials which are all capable of reacting with phosphoric and polyphosphoric acids, it is believed that the stabilizer may function, at least in part, by reacting with phosphoric and polyphosphoric acids which are present in the phosphorodithioic acid diester as impurities. Alternatively, it is possible that phosphoric and polyphosphoric acid contaminants may be derived by direct hydrolysis of the phosphorodithioic acid diesters themselves.

The following examples are intended only to illustrate the invention and are not to be construed as imposing limitations on it.

EXAMPLE I

A mixture of 6,010 grams (100 moles) of 2-propanol and 10,220 grams (100 moles) of 4-methyl-2-pentanol was added to a slurry of 11,100 grams (50 moles) of phosphorus pentasulfide in 5,000 grams of mineral oil at an initial temperature of 60° C. The temperature of the reaction mixture rose to 88° C. during addition of the alcohol mixture. When the addition was completed, the temperature of the mixture was maintained at 88° C. for an additional 2 hours. The resulting mixture was filtered to give a phosphorodithioic acid diester composition which contained 9.6% phosphorus.

EXAMPLE II

One thousand grams of the product of Example I was heated at 129° C. in a stirred three-necked flask which was equipped with a thermometer and a condenser. The top of the condenser was connected to a wet test meter for measurement of the volume of evolved gases. After 30 minutes at 129° C., a total of 1.8 liters of gas had been evolved. The experiment was terminated after 40 minutes when a total of 10.4 liters of gaseous decomposition products had been released. The rate at which these gaseous decomposition products were evolved from the heated phosphorodithioic acid diester is a measure of the compositions's thermal stability.

EXAMPLE III

Example II was repeated except that 0.15 liter (0.007 mole) of anhydrous ammonia gas was absorbed in the product of Example I at room temperature before heating the material at 129° C. A total of 0.25 liter of gas was evolved after 30 minutes at 129° C., and the experiment was terminated after 60 minutes when a total of 0.49 liters of gaseous decomposition products had been released. Comparison of these results with those of Example II demonstrates that the addition of a small amount of ammonia to the phosphorodithioic acid diester served to significantly increase the thermal stability of this material.

EXAMPLE IV

A phosphorodithioic acid diester was prepared from a mixture of 1000 grams (3.1 moles) of the product of Example I, 111 grams (0.50 mole) of phosphorus pentasulfide, and 178 grams (2.19 moles) of an equimolar mixture of 2-propanol and 4-methyl-2-pentanol by heating the mixture at 88° C. for 1.5 hours. One thousand grams of the resulting phosphorodithioic acid diester was then heated at 129° C. and the volume of the gaseous decomposition products from this material was monitored as a function of time. The total volume of gas evolved after 30 and 38 minutes was 1.95 and 11.25 liters respectively. These decomposition results are substantially the same as those which are set forth in Example II.

EXAMPLE V

A phosphorodithioic acid diester was prepared from a mixture of 1000 grams (3.1 moles) of the product of Example I, 111 grams (0.50 mole) of phosphorus pentasulfide, 178 grams (2.19 moles) of an equimolar mixture of 2-propanol and 4-methyl-2-pentanol, and 1.0 gram (0.0087 mole) of 85% phosphoric acid ($H_3PO_4$) by heating the mixture at 88° C. for 1.5 hours. One thousand grams of the resulting phosphorodithioic acid diester, which contained phosphoric acid as an impurity, was then heated at 129° C. and the volume of the gaseous decomposition products from this material was monitored as a function of time. The total amount of gas evolved after 10 and 19 minutes was 1.2 and 5.5 liters respectively. Comparison of these results with those of Example IV demonstrates that the presence of phosphoric acid serves to decrease the thermal stability of the subject phosphorodithioic acid diester.

EXAMPLE VI

A mixture of 1000 grams (3.1 moles) of the product of Example I and 1.0 gram (0.0087 mole) of 85% phosphoric acid ($H_3PO_4$) was heated at 104° C. and the volume of the gaseous decomposition products from this mixture was monitored as a function of time. The total amount of gas evolved after 20 and 40 minutes was 0.8 and 3.8 liters respectively.

EXAMPLE VII

Example VI was repeated except that the mixture additionally contained 2.5 grams (0.018 mole) of potassium carbonate. After 60 minutes at 104° C., the mixture had released a total of 0.15 liter of gaseous decomposition products.

EXAMPLE VIII

Example VI was repeated except that the mixture additionally contained 1.0 gram (0.018 mole) of calcium oxide. After 60 minutes at 104° C., the mixture had released a total of 0.10 liter of gaseous decomposition products.

EXAMPLE IX

Example VI was repeated except that the mixture additionally contained 2.0 grams (0.019 mole) of sodium carbonate. After 60 minutes at 104° C., the mixture had released a total of 0.45 liter of gaseous decomposition products.

EXAMPLE X

Example VI was repeated except that the mixture additionally contained 0.9 liter (0.04 mole) of absorbed ammonia gas. After 60 minutes at 104° C., the mixture had released a total of 0.32 liter of gaseous decomposition products.

EXAMPLE XI

Example VI was repeated except that the mixture additionally contained 1.8 liter (0.08 mole) of absorbed dimethylamine gas. After 60 minutes at 104° C., the mixture had released a total of 0.24 liter of gaseous decomposition products.

We claim:

1. A method for stabilizing a phosphorodithioic acid diester which comprises adding to said diester a stabilizer which is selected from the group consisting of ammonia, ammonium carbonate, ammonium salts of carboxylic acids, the oxides, hydroxides and carbonates of lithium, sodium, potassium, rubidium, cesium, berylium, magnesium, calcium, strontium and barium, and mixtures thereof, wherein the amount of said stabilizer is effective to increase the thermal stability of the phosphorodithioic acid diester.

2. The method as set forth in claim 1 wherein said phosphorodithioic acid diester is derived from the reaction of a phosphorus sulfide with at least one compound selected from the group consisting of alcohols and phenols.

3. The method as set forth in claim 2 wherein said phosphorodithioic acid diester is derived from the reaction of a phosphorus sulfide with a secondary aliphatic alcohol or a mixture of compounds selected from the group consisting of alcohols and phenols which comprises at least one secondary aliphatic alcohol.

4. The method as set forth in claim 3 wherein said phosphorodithioic acid diester is derived from the reaction of a phosphorus sulfide with a mixture of monohydric alcohols which comprises at least one secondary alcohol.

5. The method as set forth in claim 4 wherein said phosphorus sulfide is phosphorus pentasulfide.

6. The method as set forth in claim 5 wherein the amount of said stabilizer is in the range from about 0.0001 to about 0.2 mole per mole of said phosphorodithioic acid diester.

7. The method as set forth in claim 2 wherein said stabilizer is selected from the group consisting of the oxides, hydroxides and carbonates of lithium, sodium, potassium, rubidium, cesium, magnesium, calcium, strontium and barium.

8. The method as set forth in claim 2 wherein said stabilizer is selected from the group consisting of ammonium carbonate and ammonium salts of carboxylic acids.

9. The method as set forth in claim 2 wherein said stabilizer is ammonia.

10. The method as set forth in claim 1 wherein said phosphorodithioic acid diester contains at least about 6 carbon atoms.

11. The composition prepared by the process which comprises mixing a phosphorodithioic acid diester with a stabilizer which is selected from the group consisting of ammonia, ammonium carbonate, ammonium salts of carboxylic acids, the oxides, hydroxides and carbonates of lithium, sodium, potassium, rubidium, cesium, berylium, magnesium, calcium, strontium and barium, and mixtures thereof, wherein the amount of said stabilizer is effective to increase the thermal stability of the phosphorodithioic acid diester.

12. The composition as set forth in claim 11 wherein said phosphorodithioic acid diester is derived from the reaction of a phosphorus sulfide with at least one compound selected from the group consisting of alcohols and phenols.

13. The composition as set forth in claim 12 wherein said phosphorodithioic acid diester is derived from the reaction of a phosphorus sulfide with a secondary aliphatic alcohol or a mixture of compounds selected from the group consisting of alcohols and phenols which comprises at least one secondary aliphatic alcohol.

14. The composition as set forth in claim 13 wherein said phosphorodithioic acid diester is derived from the reaction of a phosphorus sulfide with a mixture of monohydric aliphatic alcohols which comprises at least one secondary alcohol.

15. The composition as set forth in claim 14 wherein said phosphorus sulfide is phosphorus pentasulfide.

16. The composition as set forth in claim 15 wherein the amount of said stabilizer is in the range from about 0.0001 to about 0.2 mole per mole of said phosphorodithioic acid diester.

17. The composition as set forth in claim 12 wherein said stabilizer is selected from the group consisting of the oxides, hydroxides and carbonates of lithium, sodium, potassium, rubidium, cesium, magnesium, calcium, strontium and barium.

18. The composition as set forth in claim 12 wherein said stabilizer is selected from the group consisting of ammonium carbonate and ammonium salts of carboxylic acids.

19. The composition as set forth in claim 12 wherein said stabilizer is ammonia.

20. The composition as set forth in claim 11 wherein said phosphorodithioic acid diester contains at least about 6 carbon atoms.

* * * * *